United States Patent [19]

MacConkey et al.

[11] Patent Number: 4,644,944

[45] Date of Patent: * Feb. 24, 1987

[54] MEMBRANE DISPENSING ASSEMBLY AND METHOD OF MANUFACTURE

[75] Inventors: James S. MacConkey, Winchester; Douglas F. Melville, Jr., Wakefield, both of Mass.; Edward J. Sharkany, Huntington, Conn.

[73] Assignee: Acme United Corporation, Fairfield, Conn.

[*] Notice: The portion of the term of this patent subsequent to Feb. 18, 2003 has been disclaimed.

[21] Appl. No.: 645,858

[22] Filed: Aug. 31, 1984

Related U.S. Application Data

[63] Continuation-in-part of Ser. No. 473,311, Mar. 8, 1983.

[51] Int. Cl.⁴ ............................................. A61F 13/00
[52] U.S. Cl. ................................................ 128/132 D
[58] Field of Search ............... 128/132 R, 132 D, 155, 128/156

[56] References Cited

U.S. PATENT DOCUMENTS 3,349,765 10/1967 Blanford ......................... 128/132 D Primary Examiner—C. Fred Rosenbaum
Assistant Examiner—Sherri E. Vinyard
Attorney, Agent, or Firm—Mattern, Ware, Stoltz & Fressola

[57] ABSTRACT

A pressure sensitive adhesive membrane and its cooperating, protective, underlying coated release paper are provided with retaining means and the membrane and paper layer are then formed into and maintained as a substantially cylindrical, rolled configuration, creating a unique easily handled, readily employable membrane dispensing assembly. In one embodiment, the retaining means comprises an adhesive which is applied to the non-release coated surface of the paper layer, thereby assuring maintenance of the rolled configuration while enhancing the deployability and the efficacy of the membrane. In another embodiment, a retaining band is affixed about the cylindrical, rolled pressure sensitive adhesive membrane in order to maintain the membrane in the desired rolled configuration.

12 Claims, 6 Drawing Figures

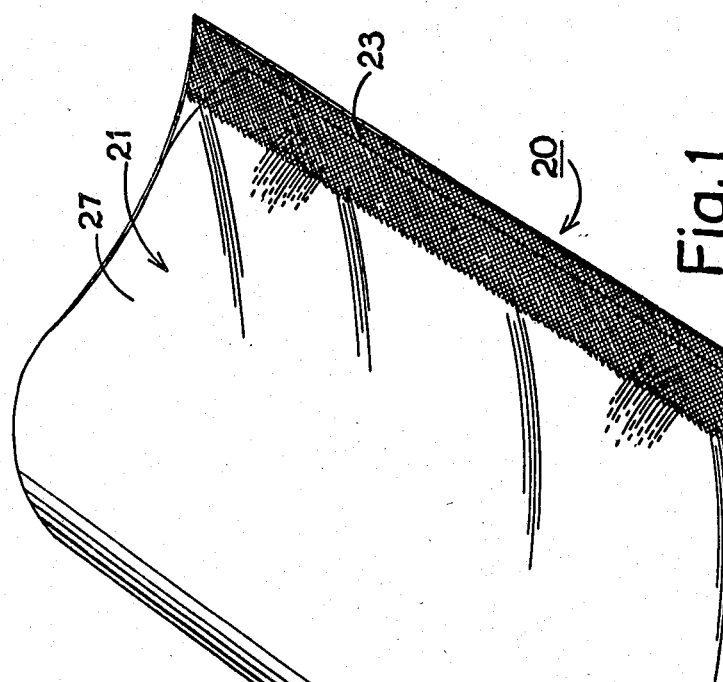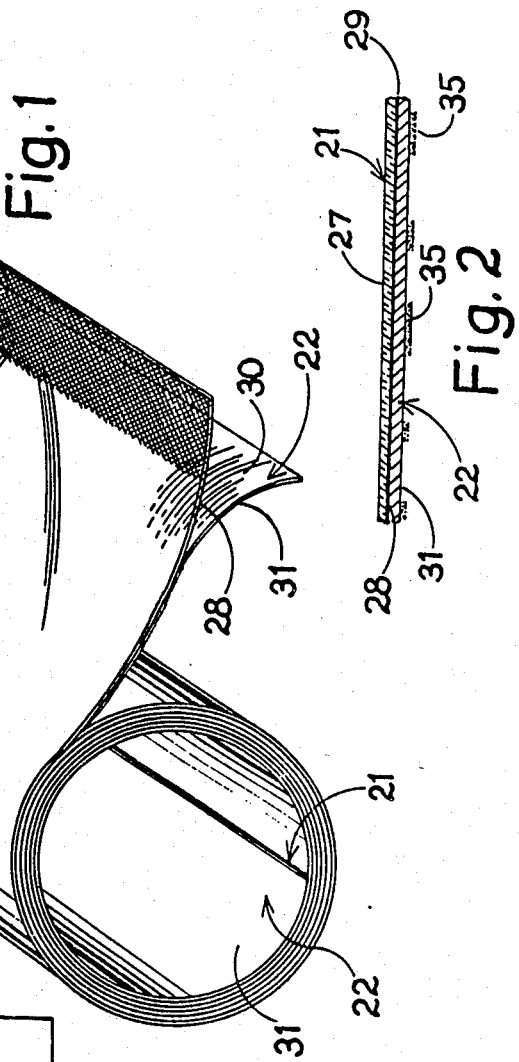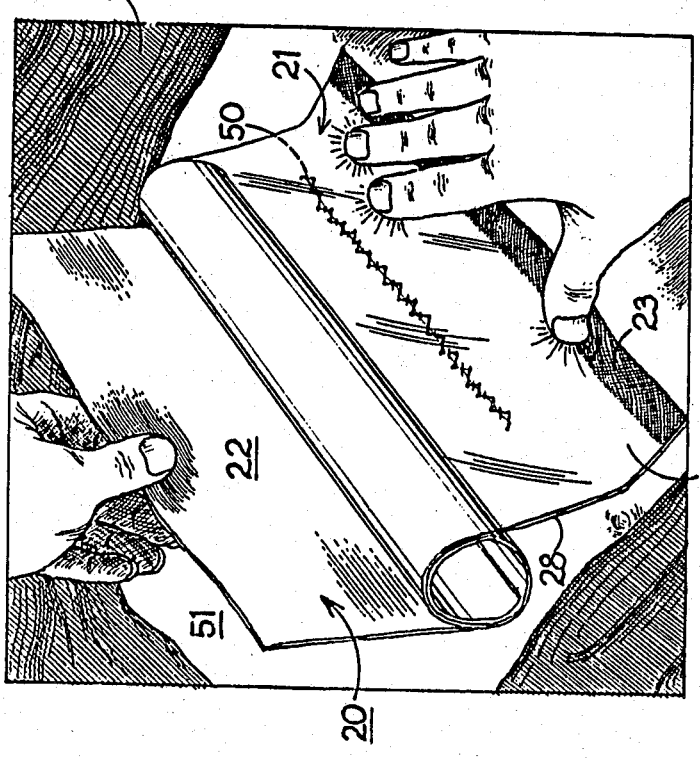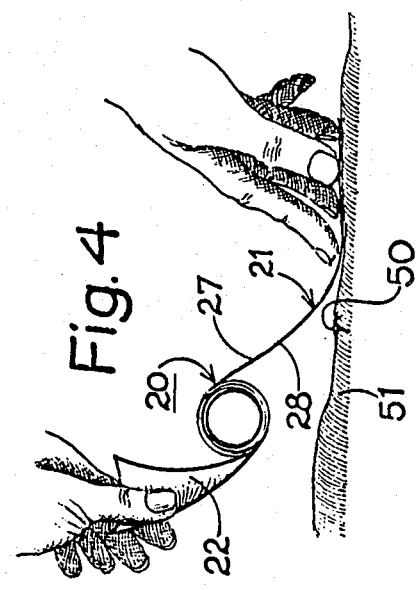

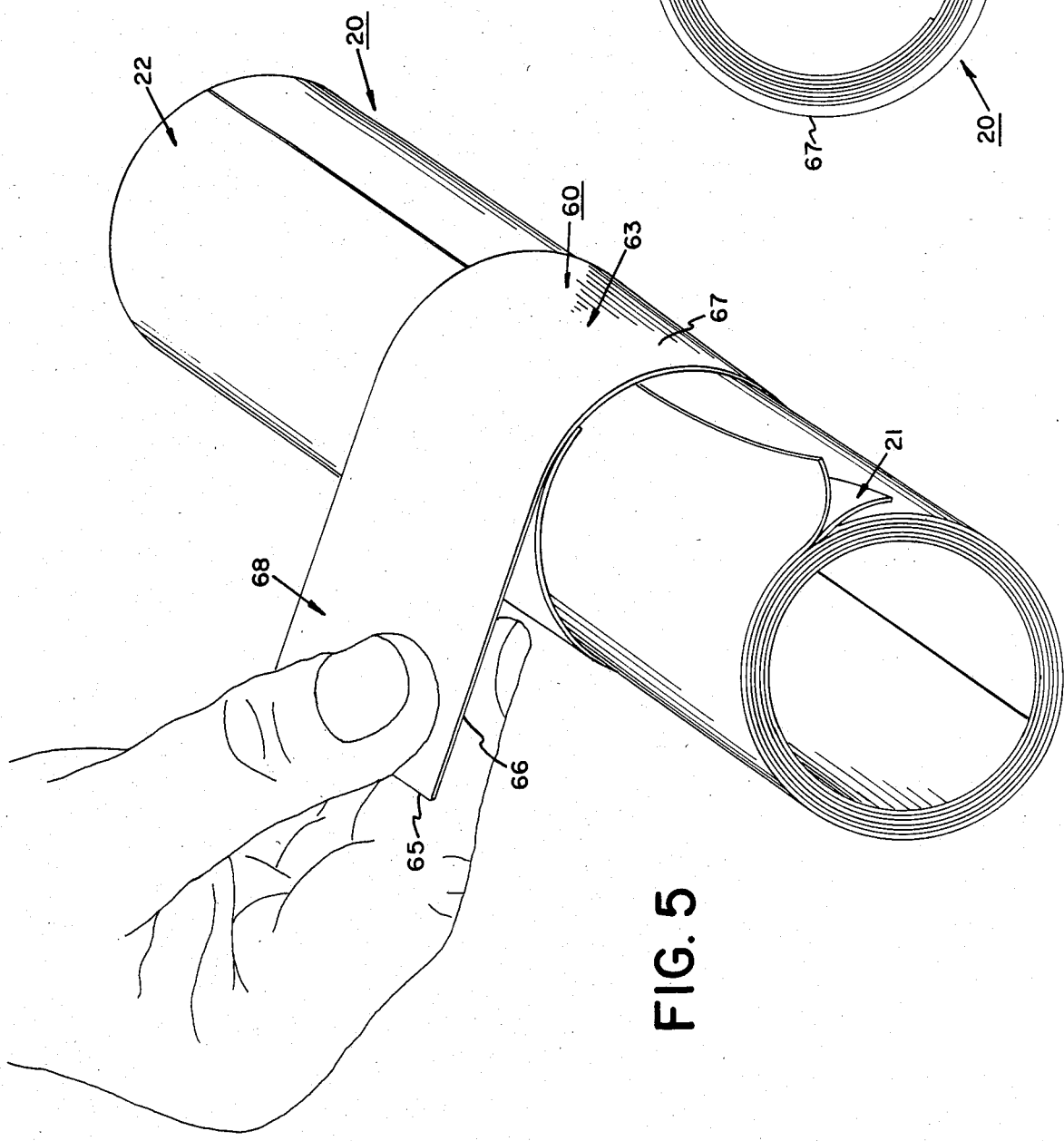

MEMBRANE DISPENSING ASSEMBLY AND METHOD OF MANUFACTURE

RELATED APPLICATION

This application is a continuation-in-part of co-pending U.S. Patent Application of Messrs. MacConkey and Melville relating to Membrane Dispensing Assembly and Method of Manufacture, bearing Ser. No. 473,311 date of Mar. 8, 1983.

TECHNICAL FIELD

This application relates to dispensing assemblies for applying pressure sensitive, adhesive, membrane materials and to methods for manufacturing the dispensing assemblies.

BACKGROUND ART

During the last several years, pressure sensitive, adhesive, vapor-permeable membranes have found increasingly greater use in the medical field as an improved surgical dressing which speeds the natural wound healing process and also protects the wound site. Although the efficacy of these vapor-permeable, adhesive membranes is widely recognized and they have now met with wide acceptance, their major drawback, not overcome before the present invention, was the difficulty encountered in applying the pressure sensitive, adhesive membranes to the patient.

Typically, these pressure sensitive, adhesive membranes are applied to the patient as a flat sheet, ranging in size from a few square inches to one or two square feet. Since these vapor-permeable, pressure sensitive, adhesive membranes are extremely thin and pliable, in order to conform to any part of the patient's body, they typically incorporate supporting backing sheets which protect the adhesive layer and are easily removed therefrom.

However, once the backing sheets are removed, as is done prior to applying the adhesive sheet to the patient, great difficulty is encountered since the sheets are extremely limp when unsupported and tend to stick to themselves. This causes major problems in separating the sheets from themselves into the flat configuration. As a result, these prior art adhesive sheets are typically not applied by a single individual, and two individuals are usually needed to assure that the adhesive sheets are stretched fully and completely, and maintained flat, so that they can be applied to the patient without problems.

Another problem encountered with prior art membranes is the tendency of the membranes to be easily overstretched during application. If this occurs, the patient experiences great discomfort, since the membranes' elastic property attempts to draw the membranes back to their original length, simultaneously pulling the patient's skin.

Although these application and handling problems have existed, no prior art system has been developed which achieves an easily handled, readily dispensible vapor-permeable, pressure sensitive, adhesive membrane capable of being used by a single individual. The only systems that have been developed require the application of additional material to the membrane itself or to the non-adhesive surface of the membrane. However, these systems suffer from a tendency to degrade the quality of the membrane, as well as introducing extra material which may interfere with the healing process or with the visibility of the wound during its healing.

Therefore, it is a principal object of the present invention to provide a membrane dispensing assembly for vapor-permeable, pressure sensitive, adhesive membranes which is quickly and easily used by a single individual, without having the membrane stick to itself.

Another object of the present invention is to provide a membrane dispensing assembly for vapor-permeable, pressure-sensitive adhesive membranes having the characteristic features described above, which achieves rapid, easy, trouble-free application to the wound site regardless of the size, shape or length of the membrane being applied to the wound.

Another object of the present invention is to provide a membrane dispensing assembly for vapor-permeable, pressure sensitive, adhesive membranes having the characteristic features defined above wherein each assembly is sized for a single, particular, surgical application, thereby being completely dispensed during that single application.

A further object of the present invention is to provide a membrane dispensing assembly for vapor-permeable, pressure sensitive, adhesive membranes having the characteristic features defined above which also assures complete sterility of the membrane for surgical use.

Another object of the present invention is to provide a membrane dispensing assembly for vapor-permeable pressure sensitive, adhesive membranes having the characteristic features defined above which prevents unwanted membrane stretching while providing continuous controlled dispensing of a taut membrane.

Other and more specific objects will in part be obvious and will in part hereinafter.

DISCLOSURE OF THE INVENTION

The present invention overcomes the prior art difficulties and drawbacks by uniquely constructing and assembling and retaining the vapor-permeable, pressure sensitive, adhesive membranes and their accompanying release-coated backing sheets in a continuous rolled form, preferably achieving a substantially cylindrical shape. By employing the rolled, cylindrically shaped dispensing assembly of this invention, the vapor-permeable, pressure sensitive, adhesive membrane layer of the system is quickly and easily applied to the desired wound site by a single individual.

This desired single-person application is achieved by the user merely holding the leading edge of the vapor-permeable, adhesive membrane in one hand and the leading edge of the release paper in the other hand. Then, the user simply pulls in opposite directions, slowly and controllably dispensing and affixing the precisely desired amount of permeable membrane to the patient.

It has been found that the rolled, substantially cylindrically shaped dispensing assembly imparts rigidity to the membrane, thereby preventing the membrane from ever becoming limp and unsupported prior to its application. By slowly unrolling and applying additional lengths of the adhesive membrane, only the amount of membrane which can be easily handled by the user is dispensed at any one time, until such time as the entire membrane has been applied to the wound site.

In addition, the membrane is always maintained taut, as is preferred, during its application to a patient due to the gentle pulling of the membrane from the rolled dispensing assembly. As a result, the membrane is incapable of being over-stretched since the membrane is never pulled from both of its ends simultaneously. In this way, all of the drawbacks, difficulties and undesirable results which have been encountered with the prior art pressure sensitive adhesive sheets are all completely eliminated.

In the preferred embodiment, every rolled, substantially cylindrical membrane dispensing assembly incorporates the optimum size and shape of membrane material which is required for a particular surgical application. In this way, the entire roll is consumed in the single application, thereby assuring that each membrane dispensing assembly once sterilized upon manufacture, is maintained sterile up to and including its time of application.

Although the rolled, substantially cylindrical membrane dispensing assembly of the present invention could incorporate standard fixed lengths or sufficient amounts of membrane for multi-uses, the preferred embodiment comprises a substantially cylindrical roll of membrane for a single application and use. This construction is preferred due to the inherent difficulty in maintaining a sterile environment for the assembly after it has been partially employed, as well as for eliminating or minimizing the amount of membrane trimming required after the membrane is in position. Since the membrane is typically applied directly to a wound or an intravenous site to assist in the healing process and maintain cleanliness, a completely sterile membrane is of the utmost importance, as well as application ease and simplicity.

In one embodiment of the present invention, the rolled, substantially cylindrically shaped dispensing assembly of the present invention is maintained by incorporating adhesive means on one surface of the backing sheet or vapor-permeable membrane.

In another embodiment, the rolled, substantially cylindrically shaped dispensing assembly of this invention is maintained in the desired configuration until use by peripherally surrounding a retaining band about the rolled dispensing assembly. Preferably, the band is centrally positioned along the length thereof and incorporates a readily accessible tab portion for quickly and easily removing the band prior to applying the membrane to the patient.

Although various band fastening means could be used, it has been found that the placement of a small drop of adhesive on the outer surface of the band prior to overlapping the band upon itself provides the most effective and economic assembly method. In this way, the band is quickly and easily secured about the cylindrically shaped membrane while also providing a readily accessible tab extension portion for facilitating removal of the band prior to use.

The invention accordingly comprises an article of manufacture possessing the features, properties and relation of elements which will be exemplified in the articles hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 1 is a perspective view of the membrane dispensing assembly of the present invention;

FIG. 2 is a cross-sectional side elevation view showing the layers forming one embodiment of the membrane dispensing assembly of the present invention;

FIG. 3 is a schematic perspective view showing the membrane dispensing assembly of the present invention in use by a single individual for a sutured wound;

FIG. 4 is a side elevation view similar to the view in FIG. 3, showing the membrane dispensing assembly of the present invention being used by a single individual for a sutured wound;

FIG. 5 is a perspective view of a second embodiment of the membrane dispensing assembly of the present invention; and FIG. 6 is an end view of the membrane dispensing assembly embodiment of FIG. 5.

BEST MODE FOR CARRYING OUT THE INVENTION

In FIG. 1, membrane dispensing assembly 20 of the present invention is shown in the preferred embodiment as a substantially cylindrically shaped, self-supported elongated roll comprising a vapor-permeable, pressure sensitive adhesive membrane layer 21 and a coated release paper layer 22 underlying in an intimate contact with membrane layer 21. Membrane layer 21 preferably incorporates an elongated holding strip 23 which is affixed to the leading edge of membrane layer 21 and, preferably, extends along substantially the entire length thereof.

Membrane layer 21 is made from vapor-permeable, pressure sensitive, adhesive material which is well known in the surgical field for use as a surgical drape or a surgical dressing. Typically the prior art pressure sensitive adhesive materials are employed directly over the patient during surgery as a drape over surgical wounds, to assist in wound healing and protection and over intravenous sites to hold the intravenous delivery system in position, while also protecting the patient from infection.

Although many various compositions have been taught for such surgical drapes and dressings, synthetic polymer sheets or films are preferred. A conventional and highly successful vapor-permeable, pressure sensitive, adhesive material of this nature, which typifies the type of material employed as membrane layer 21, is taught in Hoddson U.S. Pat. No. 3,645,835. However, any similar pressure sensitive, adhesive sheet or film can be employed with equal efficacy in the membrane dispensing assembly of the present invention.

Membrane layer 21 preferably comprises a substantially continuous, elongated thin polymer film or sheet having a first or top surface 27 and a second or bottom surface 28. First surface 27 is non-adhesive and forms the top, outside surface of the surgical drape or dressing once membrane layer 21 has been applied to the patient. Bottom surface 28 incorporates the desired pressure sensitive, adhesive material 29 thereon which achieves the desired secure affixation of membrane layer 21 to the body of the patient.

Various adhesive material can be employed for adhesive layer 29 as is disclosed in Hoddson U.S. Pat. No. 3,645,835, and other comparable prior art references. In addition, as is well known in the art, adhesive layer 29 can be applied either to the entire surface 28 or to portions thereof.

As is common in the prior art, adhesive surface 29 is protected by a layer of coated release paper 22, which has a first surface 30 and a second surface 31. First surface 30 is in intimate, protective contact with adhesive layer 29 and layer 28 of membrane 21 and incorporates a coating of release material to assure separation ease of release paper 22 from membrane layer 21, without injuring or degrading the adhesive qualities of layer 29. Such release coatings are common knowledge in the industry.

In order for the membrane dispensing assembly of the present invention to maintain its substantially cylindrical shape until the membrane is unrolled while being applied to the patient, the membrane dispensing assembly of the present invention incorporates retaining means. In one embodiment, adhesive means 35 is employed. Although adhesive means 35 may be applied to either surface 27 of membrane layer 21 or surface 31 of coated release paper 22, it is preferred that adhesive means 35 be applied to surface 31 of release paper layer 22 as shown in FIG. 2.

Preferably, adhesive means 35 comprises a low tack or slightly tacky, easily separated adhesive which is applied to surface 31 of paper layer 22 in preselected, widely spaced locations. It has been found that any pressure sensitive adhesive with low tack may be used, including natural rubber, synthetic rubber and acrylic types. One such low tack, pressure sensitive adhesive is 3M's Scotchbrand Spray Mount Adhesive #6065.

The adhesive may be applied from water or solvent by spray, roll coating, printing or other suitable method. Since adhesive means 35 is employed solely to maintain the substantially cylindrical shape of membrane dispensing assembly 20 of the present invention, it has been found that adhesive means 35 is preferably employed in limited quantities and may be applied in a pattern, dots, design, or in solid lines to either a portion of or to the entire surface 31 of paper layer 22.

In general, the amount of adhesive means 35 required depends upon the diameter desired for the membrane dispensing assembly 20, since smaller diameters require additional adhesion to be maintained. However, once the required amount of adhesive means 35 is established, adhesive means 35 can be spread in a plurality of alternate patterns or designs. If desired, thin elongated strips of adhesive material 35 can be positioned in substantially parallel strips along surface 31 of paper layer 22 to provide the required amount of adhesive material 35, with the strips extending parallel, perpendicular, or at skewed angles to the side edges of paper layer 22. Alternatively, as depicted in FIG. 2, adhesive means 35 can be spread on surface 31 of paper layer 22 in random spots or locations. If desired, adhesive means 35 can be spread uniformly over the entire surface 31 of paper layer 22.

As briefly discussed above, each membrane dispensing assembly 20 of the present invention is preferably constructed with the precise amount of pressure-sensitive adhesive membrane material required for a particular surgical application or procedure. As a result, by selecting the membrane dispensing assembly designed for a desired surgical procedure, the entire membrane material is consumed during that procedure. In this way, cumbersome and undesirable cutting or trimming of the membrane material is eliminated and complete sterility of the material being employed is maintained.

In order to manufacture the adhesively retained embodiment of membrane dispensing assembly 20 of the present invention, a prior art, conventional pressure sensitive, adhesive membrane film or sheet is obtained along with a cooperating layer of release paper in intimate, protective contact with the adhesive surface of the membrane. Preferably, the cooperating, engaging layers of the membrane and release paper are spread substantially flat and then cut to the desired size and shape necessary for a particular surgical application.

Once the desired size and shape of pressure sensitive, adhesive membrane layer 21 and release paper layer 22 are obtained, an easily separated, slightly tacky, adhesive material 35 is applied to exposed surface 31 of paper layer 22. Then, one edge of the combined, intimately engaged membrane layer 21 and release paper layer 22 are lifted, and formed into a substantially cylindrical shape, bringing surface 27 of the membrane 21 into contact with adhesive means 35 and surface 31 of paper layer 22. This step is then completed by advancing the substantially cylindrical, elongated, initially formed roll along the remaining length of the combined membrane layer 21 and paper layer 22 until the self-supporting, substantially cylindrical, elongated roll of membrane dispensing assembly 20 is complete.

As is readily apparent from the preceding description, during the rolling process, adhesive layer 35 of surface 31 of paper layer 22 is brought into contact with surface 27 of membrane layer 21 thereby preventing layers 21 and 22 from separating from each other until a separating force is applied. In this way, the desired cylindrical configuration is maintained.

Preferably, the manufacturing process is completed by packaging the membrane dispensing assembly and then sterilizing the packaged assembly for later use. In this way, the user is assured that a completely sterilized assembly is available when required.

In constructing the substantially cylindrical elongated roll of the present invention, either membrane layer 21 or paper layer 22 may form the outer peripheral surface of membrane dispensing assembly 20. It has been found that membrane dispensing assembly 20 is equally efficacious in use, regardless of which layer forms the outer surface. However, depending upon the particular embodiment being employed, one layer may be more desirable.

In the embodiment detailed above, wherein adhesive 35 is employed, it has been found that it is more advantageous to construct the cylindrical roll with membrane layer 21 forming the outer surface. This arrangement is preferred since adhesive 35 is preferably applied to surface 31 of paper layer 22 and the cylindrical construction with membrane layer 21 on the outside assures complete adhesion of the entire length of material as well as eliminating any possiblity that adhesive 35 will be present along the outer peripheral surface of the cylindrical roll.

In FIG. 5 and 6, another embodiment is shown for the retaining means employed to maintain the membrane dispensing assembly of the present invention in the desired substantially cylindrical shape. In this embodiment, membrane dispensing assembly 20 incorporates the pressure sensitive adhesive membrane layer 21, the coated release paper layer 22 underlying membrane layer 21 in intimate contact therewith. In addition, elongated holding strip 23 is preferably affixed to membrane layer 21 along the leading edge of membrane layer 21, extending substantially along the entire length thereof. As previously detailed, membrane dispensing assembly 20 of this invention is formed in a substantially cylindrically shaped, self-supporting, elongated roll configuration. However, in this embodiment, the cylindrical roll is formed without the use of adhesive 35.

In this embodiment, membrane dispensing assembly 20 incorporates a peripherally surrounding, roll-retaining band 60. Preferably, band 60 is positioned substantially mid-way along the length of the substantially cylindrically shaped, self-supporting, elongated roll and is mounted thereabout in the manner so that a portion of band 60 overlies itself and is retained in the overlying position by suitable retaining means 61. Preferably, retaining band 60 comprises a single, narrow, elongated strip of material 63 which peripherally surrounds and securely holds the combined elongated, substantially cylindrically-shaped membrane layer 21 and paper layer 22 of dispensing assembly 20 in the desired cylindrical configuration.

In this embodiment, it has been found that the substantially cylindrical roll is preferably formed with paper layer 22 forming the outer peripheral surface. Since adhesive 35 is not employed, the reasons detailed above are not applicable to this embodiment. Furthermore, it has been found that when paper layer 22 comprises the outer peripheral surface of membrane dispensing assembly 20, paper layer 22 provides a protective shield for the more fragile membrane layer 21, thereby preventing any possible unwanted damage to membrane layer 21, such as folding, wrinkling, creasing, etc.

As shown in FIGS. 5 and 6, elongated strip 63 comprises terminating edges 64 and 65, an inner surface 66, and an outer surface 67. Band 60 is wrapped about the outer, exposed surface of paper layer 22 so that edge 64 of strip 63 is in underlying, retained abutting engagement with inner surface 66 of strip 63.

In the preferred construction, retaining band 60 also comprises fastening means 61 positioned between outer surface 67 and inner surface 66 of elongated strip 63 in the area directly adjacent edge 64 in which surface 66 contacts surface 67. In this way, retaining band 60 is securely affixed to itself in a self-supporting securely maintained configuration, peripherally surrounding paper layer 22 of membrane dispensing assembly 20, maintaining the desired cylindrically shaped roll configuration. In the preferred embodiment, fastening means 61 comprises a small quantity of glue or adhesive. However, any other suitable, quick disconnect fastener could be employed.

In the preferred construction, retaining band 60 is also constructed with a tab portion 68 formed between fastening means 61 and terminating edge 65. Tab portion 68 provides a readily accessible, easily employed section of material by which the user can quickly and easily remove retaining band 60 from paper layer 22 of membrane dispensing assembly 20. Typically, tab portion 68 is merely lifted and pulled away from paper layer 22, by simply breaking or separating fastening means 61, thereby causing surface 66 to be separated from surface 67 in the area adjacent edge 64. In this way, retaining band 60 is easily removed from its securely retained, peripherally surrounding position about paper layer 22 of membrane dispensing assembly 20.

As previously discussed in regard to the alternate embodiment for membrane dispensing assembly 20 of the present invention, it is preferred that the precise amount of pressure-sensitive adhesive membrane material required for a particular surgical operational procedure is employed. Similarly, in order to manufacture this embodiment of membrane dispensing assembly 20, the substantially identical steps detailed above in regard to the alternate embodiment are employed, except that adhesive means 35 is not used and the cylindrical roll is preferably formed with paper layer 22 as the outer layer. However, all of the other steps detailed above in regard to the achievement of a substantially cylindrical, elongated roll formation are used.

In addition, once the desired cylindrically shaped roll is attained, the assembly is completed by peripherally surrounding the substantially cylindrically-shaped elongated roll with retaining band 60. In the preferred procedure, edge 64 is placed in contact with paper layer 22 of membrane dispensing assembly 20 with inner surface 66 contacting paper layer 22. Then, the elongated strip 63 is wrapped and securely affixed about the elongated, cylindrically-shaped roll, thereby forming membrane dispensing assembly 20.

In the preferred embodiment, band 60 is affixed about paper layer 22 by employing an adhesive. It has been found that band 60 is most economically and efficaciously secured in position by dropping a small quantity of hot glue onto outer surface 67 of strip 63 directly adjacent to edge 64, just prior to bringing elongated strip 63 into overlying, contacting engagement with edge 64 and surface 67 in the area directly adjacent edge 64. Then, as inner surface 66 contacts glue 61, the desired adhesion between surfaces 66 and 67 is achieved, with the remainder of strip 63 forming tab portion 68. Once this manufacturing process has been completed, membrane dispensing assembly 20 of this embodiment is ready for sterilization and packaging.

Regardless of which embodiment of membrane dispensing assembly 20 of the present invention is employed, the application procedures and advantages attained are identical. However, as is readily apparent from the preceding description concerning the embodiment of membrane dispensing assembly 20 which incorporates retaining band 60, band 60 must be removed in the manner detailed above prior to applying the membrane to the particular wound site.

It has been found that the advantages attained from employing the membrane dispensing assembly of this invention are identical, regardless of the embodiment used, since the elongated, substantially cylindrically-shaped rolled configuration, once formed and retained for the period of time typically encountered during sterilization and storage prior to use, causes membrane layer 21 and paper layer 22 to be retained in the rolled, substantially cylindrically-shaped configuration. Consequently, when the embodiment employing retaining band 60 is used and band 60 is removed prior to the application of the membrane layer to the wound site, the layers forming the substantially cylindrically shaped rolled configuration retain the cylindrical shape until the application procedures are completed. Consequently, the ease of application detailed below is attained.

By referring to FIGS. 3 and 4, along with the following detailed discussion, the ease of application and use of membrane dispensing assembly 20 of the present invention can best be understood. As shown in FIGS. 3 and 4, a sutured wound 50 is diagrammatically depicted on the torso 51 of a patient, with the wound site being peripherally surrounded by drapes 52. Membrane dispensing system 20 of the present invention is shown in the process of being applied over sutured wound 50, in its typical manner by a single individual with ease and simplicity.

In order to employ membrane dispensing assembly 20 of this invention, the user initially holds elongated, edge-mounted holding strip 23 of membrane layer 21 in one hand, while holding the edge of release paper 22 in the other hand. Then, a small portion of the vapor-permeable, pressure sensitive adhesive membrane 21 is removed from the release paper 22. With release paper 22 in one hand and holding strip 23 in the other hand, membrane layer 21 is oriented into the precisely desired position above the wound site and then the exposed adhesive surface 28 of membrane 21 is applied to the patient's torso 51.

As clearly depicted in FIGS. 3 and 4, the user then merely pulls the release paper 22 with one hand with the desired amount of force to dispense an additional length of membrane 21, while simultaneously advancing the user's other hand over surface 28 of membrane 21 to securely adhere adhesive layer 28 of membrane 21 to torso 51 of the patient. This controlled, easily handled, dispensing procedure is continued until the entire length of membrane 21 has been fully dispensed and applied to the patient in the precisely desired position.

Once membrane 21 is quickly and easily affixed to the patient's torso 51 in the manner described above, completely covering and protecting the wound site, such as sutured wound 50, holding strip 23 is cut away and removed from the patient, since this optional, edge-mounted holding strip 23 does not form part of the wound closure, healing membrane.

By employing the rolled, substantially cylindrically shaped membrane dispensing assembly 20 of the present invention, pressure sensitive, adhesive film or membrane 21 is maintained rigid throughout the entire application procedure, thereby eliminating the prior art difficulties encountered with unsupported, limp membranes or films. In addition, membrane 21 is taut throughout the application procedure, while simultaneously being incapable of being overstretched. As a result, patient discomfort experienced from the application of overstretched prior art membranes is also totally eliminated.

As is readily apparent from the preceding description, by employing the membrane dispensing assembly of this invention, a single user can quickly and easily apply any desired length of vapor-permeable, pressure sensitive, adhesive membrane to a patient. In addition, by employing the membrane dispensing assembly of this invention, all of the prior art undesirable self-adhering tendencies are eliminated, as well as the conventional need for two individuals to securely and precisely position a membrane in the desired location. Moreover, the membrane dispensing assembly of this invention provides a compact package which is more easily handled and maintained completely sterile prior to its use.

It will thus be seen that the objects set forth above, among those made apparent from the preceding description, are efficiently attained and, since certain changes may be made in the above article without departing from the scope of invention, it is intended that all matter contained in the above description are shown in the accompanying drawings shall be interpreted as illustrative and not in a limiting sense.

It is also to be understood that the following claims are intended to cover all of the generic and specific features of the invention herein described, and all statements of the scope of the invention, which as a matter of language, might be said to fall therebetween:

Having described our invention, what we claim is new and desire to secure by Letters Patent is:

1. An easily handled, readily employable membrane dispensing assembly comprising
   A. a self-supporting, self-contained, substantially cylindrically shaped roll incorporating
      1. a first layer formed by a pressure sensitive adhesive membrane and
      2. a second layer formed by a coated release paper, the coated surface of which is in intimate protective contact with the adhesive surface of the membrane; and
   B. retaining means comprising a band peripherally surrounding the substantially cylindrically shaped roll and maintaining said cylindrically shaped roll in the desired configuration.

2. The membrane dispensing assembly defined in claim 1, further comprising
   C. an elongated holding strip mounted along the leading edge of the membrane layer, providing a convenient edge mounted membrane holder for assisting in the dispensing, handling and application of the membrane to the desired surface.

3. The membrane dispensing assembly defined in claim 2, wherein the assembly is further defined as comprising a membrane layer having an overall, fully dispensed size and shape which is equivalent to the requirements for a specific, single type of surgical application, thereby assuring the complete dispensing and use of the entire quantity of membrane material contained therein.

4. The membrane dispensing assembly defined in claim 3, wherein said assembly is further defined as being sterilized and maintained in a sterile envelope until use.

5. The membrane dispensing assembly defined in claim 1, wherein said band is further defined as comprising an elongated strip of material having a first, inwardly-facing surface and a second, outwardly-facing surface, with said first surface being in peripheral surrounding engagement with the outer peripheral surface of the cylindrically shaped roll and in overlying contacting engagement with a portion of the second surface, thereby assuring complete, surrounding, retained engagement of the substantially cylindrically shaped roll.

6. The membrane dispensing assembly defined in claim 5, wherein the band is further defined as comprising fastening means positioned between the first and second contacting surfaces of the band, thereby maintaining said contacting portions in secure, interengagement.

7. The membrane dispensing assembly defined in claim 6, wherein said fastening means is further defined as comprising a glue which is responsive to a pulling force for easy separation.

8. The membrane dispensing assembly defined in claim 7, wherein said band is further defined as comprising a tab portion forming a part thereof and extending from the intimately engaged, glued surfaces thereof, providing a readily accessible, easily employable portion for disconnecting the band from its peripherally surrounding roll configuration retaining position, when disconnection is desired.

9. A method for manufacturing an easily handled, readily employable membrane dispensing assembly comprising the steps of:
   A. obtaining a combined, intimately engaged wound dressing comprising a pressure sensitive, adhesive membrane layer and a coated release paper layer overlying and in intimate, protective contact with the adhesive surface of the membrane layer;

B. cutting the wound dressing to a desired size and shape which represents a particular size and shape for which the membrane layer would be used in a particular surgical application;

C. rolling the entire wound dressing into a substantially cylindrically shaped configuration; and D. positioning a rolled configuration securing band about a portion of the outer peripheral surface of the cylindrically shaped roll, thereby forming the membrane dispensing assembly.

10. The method defined in claim 9, wherein the rolling step is further defined as comprising the steps of:

1. lifting the terminating edge of the wound dressing;
2. wrappingly placing the terminating edge of the paper layer of the wound dressing in contact with the exposed surface of the membrane layer, thereby forming an initial, substantially cylindrical roll shape; and
3. advancing the initially formed roll configuration along the remaining wound dressing, thereby attaining the desired substantially cylindrically shaped roll configuration.

11. The method defined in claim 10, wherein the band securing step is further defined as comprising the steps of:

1. positioning the leading edge of the elongated strip forming the band in contact with the outer peripheral surface of the cylindrically shaped roll,
2. wrappingly surrounding the elongated strip forming the retaining band about the outer peripheral surface of the elongated, substantially cylindrically shaped roll;
3. applying adhesive means to the outer surface of the elongated strip forming the retaining band in a position in juxtaposed adjacent relationship to the leading edge of said band; and
4. wrappingly advancing the elongated strip about one entire section of the substantially cylindrically shaped roll and wrappingly advancing the elongated strip about itself, bringing a portion thereof into contacting engagement with the leading edge of the strip and the adhesive means adjacent the leading edge, thereby securely affixing the band to itself and providing the desired secure retention of the substantially cylindrically shaped roll configuration, achieving the desired membrane dispensing assembly.

12. The method defined in claim 11, further comprising the step of:

5. forming an elongated strip having a length sufficient to incorporate a readily accesible, band breaking tab portion extending from the terminating edges of the adhesive means.

* * * * *